United States Patent [19]

Johnsen

[11] Patent Number: 5,549,588

[45] Date of Patent: Aug. 27, 1996

[54] COUPLING DEVICE FOR OSTOMY POUCH

[75] Inventor: Kenneth A. Johnsen, Piscataway, N.J.

[73] Assignee: E. R. Squibb & Sons, Inc., Princeton, N.J.

[21] Appl. No.: 289,821

[22] Filed: Aug. 12, 1994

[51] Int. Cl.⁶ ........................................................ A61F 5/44
[52] U.S. Cl. .......................... 604/339; 604/342; 604/338
[58] Field of Search .................................... 604/338, 339, 604/342

[56] References Cited

U.S. PATENT DOCUMENTS 5,269,773  12/1993  Vidal ........................................ 604/342
5,356,399  10/1994  Takahashi ................................ 604/338

FOREIGN PATENT DOCUMENTS 2179556  3/1987  United Kingdom ................... 604/342

Primary Examiner—Mary Beth Jones
Assistant Examiner—Mark O. Polutta
Attorney, Agent, or Firm—Stuart E. Kreiger

[57] ABSTRACT

The coupling device for an ostomy pouch includes a flexible, deflectable, annular force transmitter member joined to an abdominal mounting plate that has a coupling member. The force transmitter member can be pulled in a direction away from the mounting plate during coupling of an ostomy pouch. The force transmitter member can thus oppose and neutralize a coupling force that is directed to the mounting plate and protect the abdomen from receiving the pressure due to the coupling force.

5 Claims, 4 Drawing Sheets

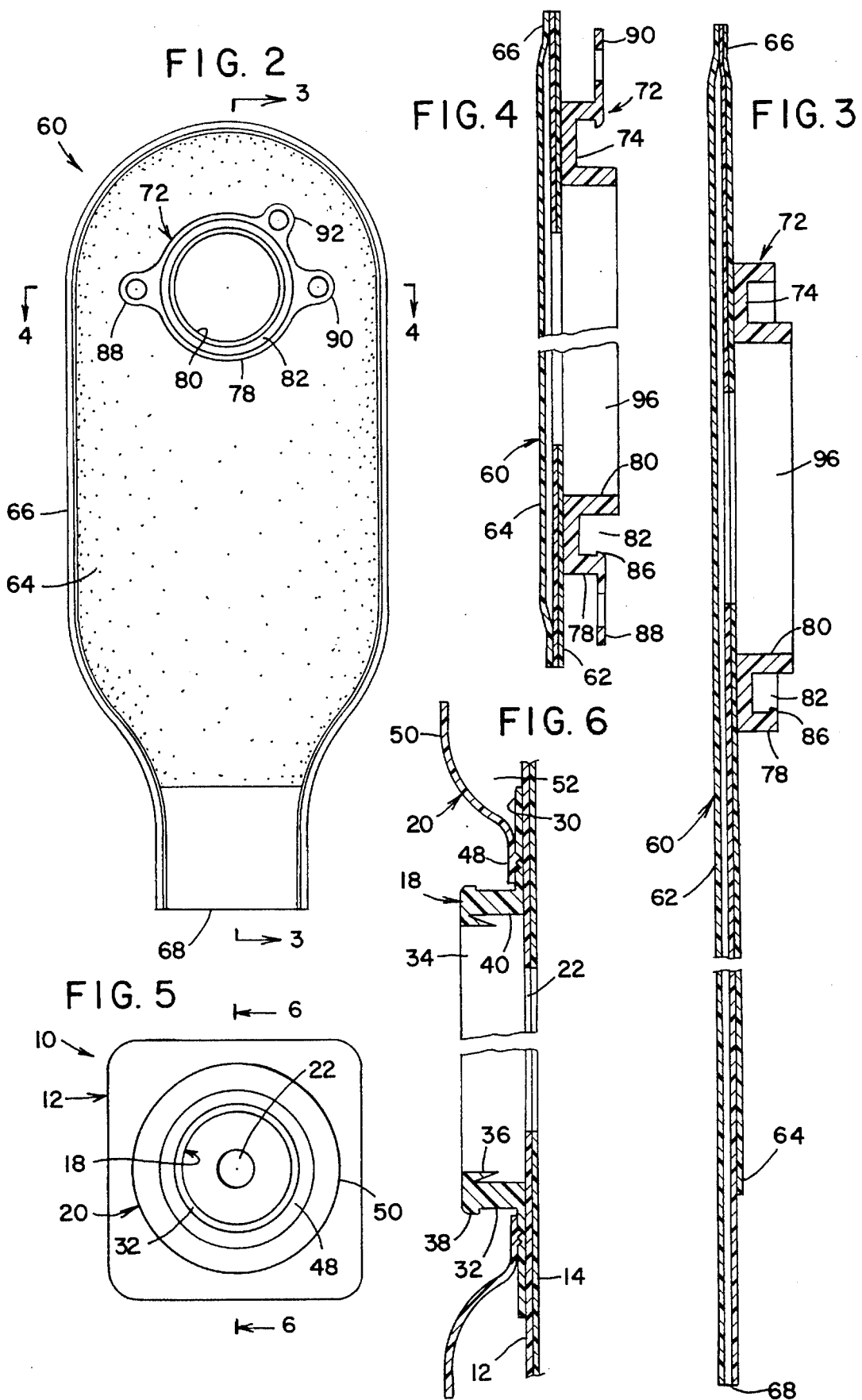

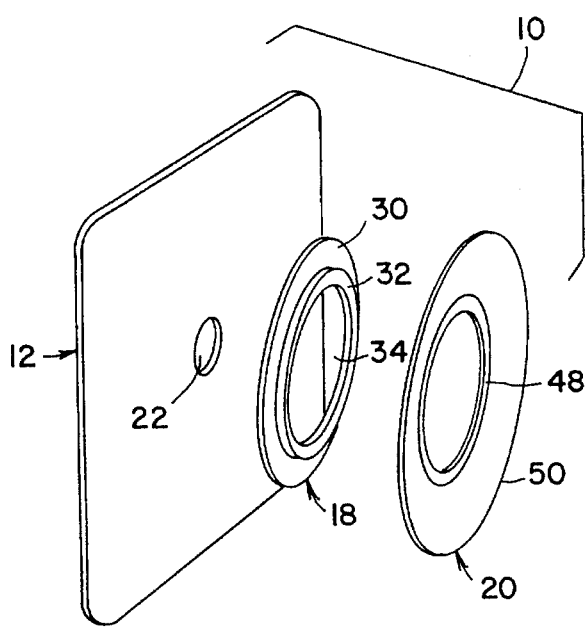
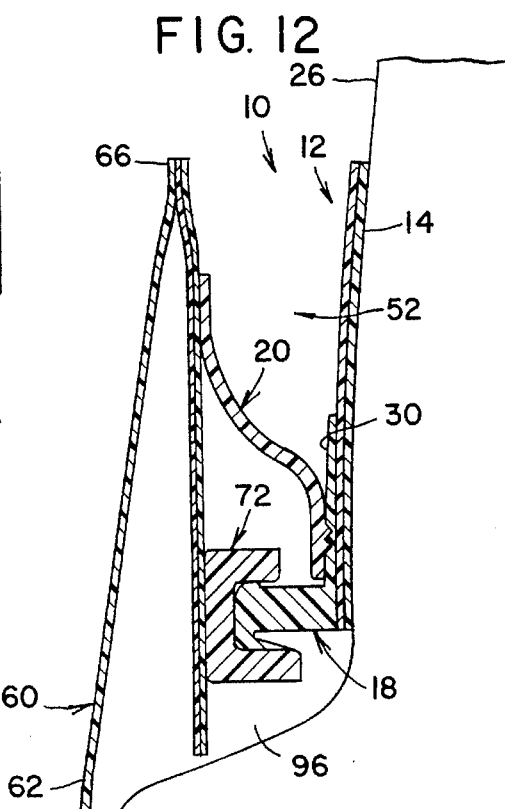
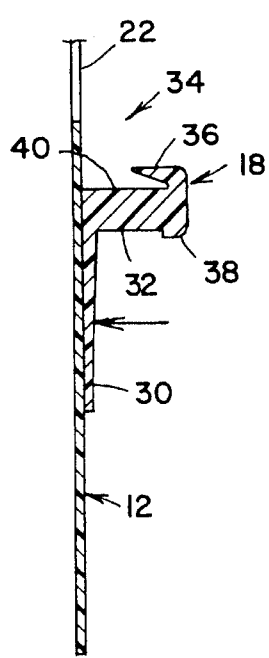
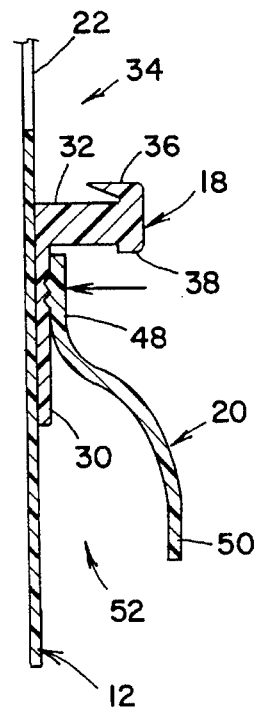
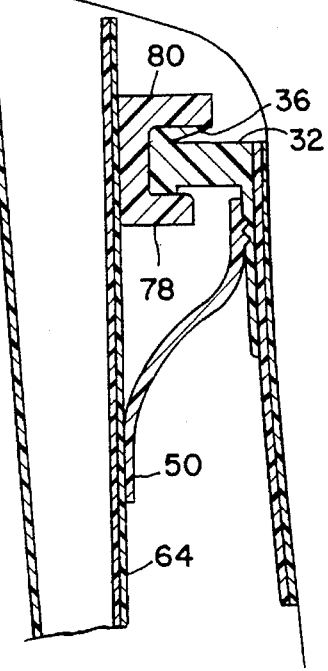

COUPLING DEVICE FOR OSTOMY POUCH

BACKGROUND OF THE INVENTION

This invention is directed to ostomy pouches and more particularly to a novel coupling device for an ostomy pouch.

Ostomy pouches are often supported at an abdominal area of the wearer for communication with a stoma that is provided in the abdomen. The support arrangement usually includes a coupling member on the ostomy pouch that is engageable with a coupling member on an abdominal mounting plate assembly that is adhered to the abdomen. The abdominal mounting plate assembly includes an opening for the stoma to enable the stoma to communicate with the ostomy pouch. Since the ostomy pouch is periodically emptied or replaced, it is desirable that the pouch be easily separated from the mounting plate assembly.

Generally the stoma and the abdominal area around the stoma are extremely sensitive to pressure and to contact of any kind. In addition, the stoma and the area around the stoma can easily become irritated, especially if there is frequent removal and replacement of an adhesive mounting plate assembly. Periodic coupling and removal of an ostomy pouch from the mounting plate assembly can result in pressure being imposed on the stoma and on portions of the abdomen that surround the stoma. Such pressure can be discomforting, especially in an area that is extremely sensitive and subject to irritation.

As shown in the prior art, an ongoing effort exists to develop coupling systems for ostomy pouches that permit forces normally transferred to or from the abdominal area to be redirected away from the stoma or substantially neutralized so that there is a minimal resultant force on the abdominal area.

For example, U.S. Pat. No. 4,419,100 shows a coupling system for an ostomy pouch wherein a coupling ring associated with a mounting plate, also referred to as a body-side coupling ring, is hinged to the mounting plate by a web. The body-side coupling ring is thus movable with respect to the mounting plate and with respect to the stoma. The web-like hinge permits placement of fingers behind the movable body-side coupling ring. The fingers at the rear of the coupling ring can apply a force from the rear of the body-side coupling ring to the front of the body-side coupling ring, while an opposing coupling force is directed from the front of the body-side coupling ring to the rear of the body-side coupling ring. The applied force at the rear of the body-side coupling ring is intended to neutralize the opposing force to avoid having a net force reach the abdominal area.

One of the problems with a hinge support for a body-side coupling ring is that it permits relative movement between the coupling members and the stoma. Such relative movement can cause irritation and unwanted contact with the stoma. Other variations of a hinge or web supported coupling member are shown in U.S. Pat. Nos. 4,786,285 and 4,973,323.

U.S. Pat. No. 4,781,708 shows an adaptor coupling secured to a pouch coupling before the pouch coupling is joined to a body-side coupling. The adaptor coupling has a substantially rigid flange that can be finger supported to deflect force from the abdomen when the coupling members are connected. However, this device necessitates that the user obtain a pouch with an adaptor member or at least obtain an adaptor member that can be secured to the pouch in order to support the pouch coupling during connection of the pouch to a body-side coupling.

Other known ostomy pouch coupling arrangements are shown in U.S. Pat. Nos. 4,559,048; 4,701,169; 4,828,553; 4,834,731; 4,889,534; 5,125,917. Several of these patents disclose devices that require forces of engagement and disengagement to be directed toward or away from the center line of the stoma making it difficult to oppose or neutralize coupling forces that may be inadvertently directed toward the abdomen.

It is thus desirable to provide a coupling device for an ostomy pouch that is affixed to a mounting plate assembly and can be used to neutralize the forces applied during connection of a body-side coupling to a pouch coupling and thus protect the abdomen and stoma from receiving the pressure due to a coupling force.

OBJECTS AND SUMMARY OF THE INVENTION

Among the several objects of the invention may be noted the provision of a novel coupling device for an ostomy pouch, a novel coupling device for an ostomy pouch having a force transmitter member, a novel coupling device wherein a force transmitter member surrounds a coupling member of the coupling device, a novel coupling device for an ostomy pouch having a force transmitter member that is secured directly to a coupling member of the coupling device, a novel coupling device having a flexible, deflectable force transmitter member that can be pulled away from the abdominal area and a novel method of opposing a force that is directed through a coupling device.

Other objects and features of the invention will be in part apparent and in part pointed out hereinafter.

In accordance with the invention, a mounting plate assembly for an ostomy pouch includes a flexible mounting plate with an opening for a stoma. A coupling member is joined to the mounting plate around the stoma opening. The coupling member has an annular rim projecting away from the mounting plate. Latch elements are provided on the annular rim to engage with corresponding latch elements on a corresponding coupling member provided on an ostomy pouch.

A flexible, deflectable annular force transmitter member is joined to the mounting plate around the annular rim of the coupling member. The force transmitter member has an inside diameter portion that is fixed to the mounting plate. An outside diameter portion of the force transmitter member is freely deflectable toward and away from the mounting plate.

The deflectable outside diameter portion of the force transmitter member constitutes a gripping portion that is finger engageable and manually grippable to transmit force through the annular rim of the coupling member. Forces transmitted through the force transmitter member to the annular rim of the coupling member neutralize opposing forces imposed on the rim when coupling of the ostomy pouch to the mounting plate assembly is performed.

The force transmitter member thus permits the user to pull the mounting plate and the mounting plate coupling member in a direction away from the abdominal wall. Such pulling enables the wearer to neutralize a coupling force that is directed against the abdominal wall when a pouch is coupled to the mounting plate assembly. Therefore, when the ostomy pouch is coupled to the mounting plate assembly the abdomen is substantially isolated from pressures attributable to the coupling force.

The invention accordingly comprises the constructions and method hereinafter described, the scope of the invention being indicated in the claims.

DESCRIPTION OF THE DRAWINGS

In the accompanying drawings,

FIG. 2 is a plan view of the ostomy pouch;

FIG. 3 is a sectional view taken on the line 3—3 of FIG. 2;

FIG. 4 is a sectional view taken on the line 4—4 of FIG. 2;

FIG. 5 is a plan view of the abdominal mounting plate assembly;

FIG. 6 is a sectional view taken on the line 6—6 of FIG. 5;

FIG. 7 is an exploded perspective view of the abdominal mounting plate assembly;

FIG. 8 is an enlarged fragmentary sectional view of the mounting plate and coupling ring thereof prior to incorporation of a force transmitter member;

FIG. 9 is a view similar to FIG. 8 with assembly of the force transmitter member;

Corresponding reference characters indicate corresponding parts throughout the several views of the drawings.

DETAILED DESCRIPTION OF THE INVENTION

Figure 1:
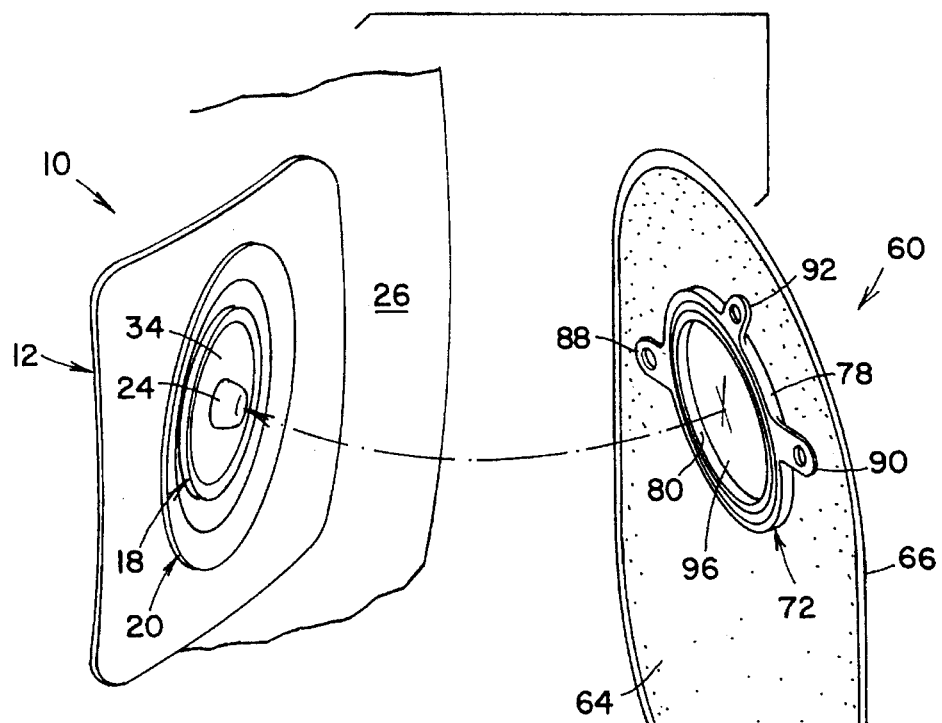
FIG. 1 is a simplified perspective view of an ostomy pouch prior to connection to an abdominal mounting plate assembly which incorporates one embodiment of the present invention.

A stomal or abdominal mounting plate assembly incorporating one embodiment of the invention is generally indicated by the reference number 10 in FIG. 1.

Figure 11:
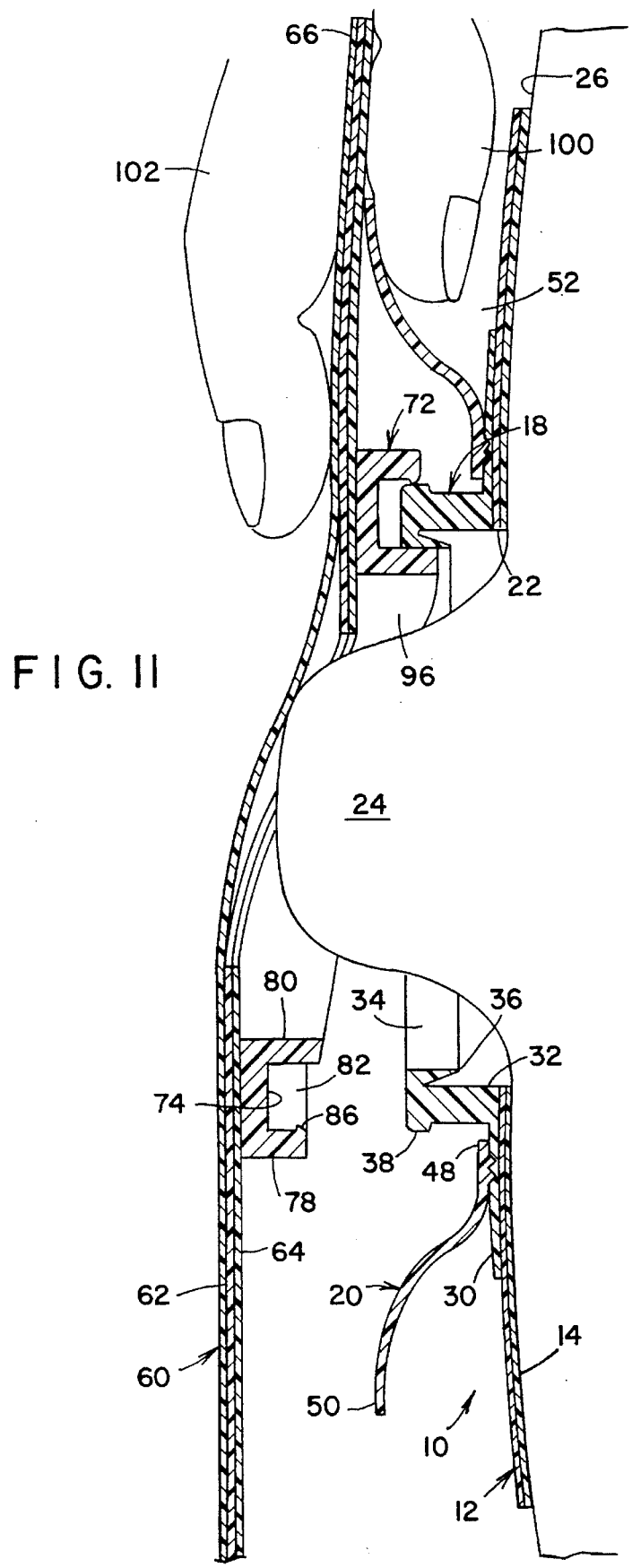
FIG. 11 is an enlarged fragmentary sectional view thereof during the assembling process shown in FIG. 10 and, FIG. 12 is a view similar to FIG. 11 after the assembling process is completed.

The mounting plate assembly 10 includes a flexible mounting plate 12 having an adhesive backing 14 shown most clearly in FIGS. 6, 11 and 12. The mounting plate 12 and the adhesive backing 14 are known constituents. Preferably the mounting plate 12 is formed of a plastic material capable of being heat-welded with other plastic material.

The mounting plate assembly 10 further includes an annular coupling member 18 preferably formed of plastic and heat-welded to the mounting plate 12. A flexible force transmitter member 20, also formed of plastic, surrounds the coupling member or coupling ring 18 and is joined with the coupling ring 18 to the mounting plate 12, preferably by ultrasonic welding.

The mounting plate assembly 10 includes an opening 22 sized to receive a stoma 24 when the mounting plate assembly 10 is adhered to an abdominal surface 26.

Referring to FIGS. 7, 8 and 9, the mounting plate 12 of the mounting plate assembly 10 is of generally rectangular shape, and the opening 22 is formed in a central portion of the mounting plate 12. The coupling ring 18 includes an annular base flange 30 that is bonded or ultrasonic welded in any suitable known manner to the mounting plate 12 to surround the opening 22. An annular rim 32 of the coupling ring 18 projects away from the base flange 30 from an inner diametrical portion of the flange 30.

The annular rim 32 defines an opening 34. A depending tooth-like projection 36 at a free end of the rim 32 projects into the opening 34. The tooth-like projection 36 is resilient and normally positioned at an angle to an inside surface 40 of the rim 32. An annular stub-like projection 38 is provided on an outside surface 40 of the rim 32 at a free end of the rim.

The force transmitter member 20 is of annular, washer-like form and includes an inner diameter portion 48 bonded or heat-welded to the base flange 30 to closely encircle the annular rim 32. An outer diameter portion 50 of the force transmitter member 20 curves away from the mounting plate 12 and is freely deflectable with respect to the mounting plate 12.

The force transmitter member 20 is substantially dish-shaped in cross-section, such that there is normally a space 52 between the outside diameter portion 50 and the mounting plate 12. The space 52 facilitates insertion of a finger or fingers between the force transmitter member 20 and the mounting plate 12.

An ostomy pouch 60 adapted to be supported on the mounting plate assembly 10 includes a front wall 62 that faces away from the abdomen 26 and a rear wall 64 that confronts the abdomen when the pouch is installed. The front and rear walls 62 and 64 are joined together by a peripheral thermo-weld 66. An unwelded portion 68 at the bottom of the pouch 60 defines a drainage opening. A known removable and reusable clip device (not shown) closes the drainage opening 68 when the pouch 60 is being worn.

The pouch 60 further includes an annular coupling ring 72 on the rear wall 64. The coupling member or coupling ring 72, which is formed of plastic, includes an annular base surface 74 that is bonded or heat-welded to the rear wall 64 of the pouch 60. An annular rim 78 that projects from the base surface 74 defines an outside diametrical portion of the coupling ring 72. Another annular rim 80 spaced from the annular rim 78 and also projecting from the base surface 74 defines an inside diametrical portion of the coupling ring 72. The annular rim 80 projects beyond the annular rim 78.

A coupling recess 82 is thus defined between the annular rim portions 78 and 80. The annular rim 78 includes an annular projection 86 that projects into the coupling recess 82.

A pair of oppositely disposed lateral flanges 88 and 90 are formed on the annular rim 78 for attachment to a support belt (not shown) that can be worn at the option of he user. A further lateral flange 92 is provided on the annular rim 78 to facilitate manipulation of the coupling ring 72, as for example when the coupling ring 72 is disengaged from the coupling ring 18.

The annular rim 78 surrounds an opening 96 that is formed in the rear wall 64 of the pouch 60 to accommodate the stoma 24 when the pouch 60 is supported on the mounting plate assembly 10.

The annular rim 32 of the coupling ring 18 on the mounting plate assembly 10 is sized to press into the coupling recess 82 of the coupling ring 72. When the coupling rings 18 and 72 are engaged, as shown in FIG. 12, the stub projection 38 of the coupling ring 18 latches beneath the stub projection 86 of the coupling ring 72. In addition, the tooth-like projection 36 of the coupling ring 18 bears against the annular rim 80 to provide a secure coupling engagement.

When the ostomy pouch 60 is to be supported on the mounting plate assembly 10, the coupling ring 72 of the ostomy pouch 60 is normally pressed onto the coupling ring 18 of the mounting plate assembly 10. During such coupling engagement, the forces applied to the coupling ring 72 against the coupling ring 18 are directed in an axial direction relative to the stoma 24 and the opening 22 in the mounting plate assembly 10.

Coupling engagement forces are thus normally imposed on the abdominal area 26 around the stoma 24. Such forces can cause discomfort to the user of the ostomy pouch 60.

Figure 10:
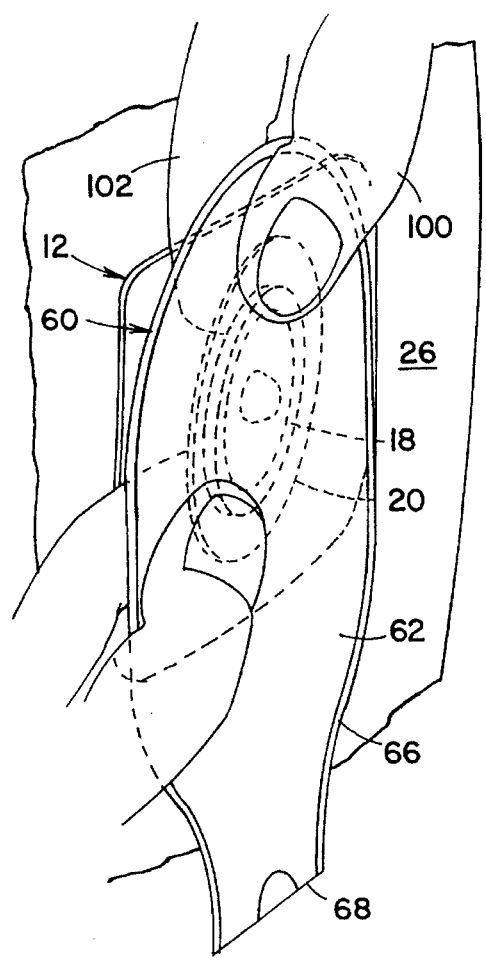
FIG. 10 is a schematic perspective view of the ostomy pouch being assembled to the abdominal mounting plate assembly.

The force transmitter member 20 enables the user to insert a thumb 100, for example, in the space 52 between the force transmitter member 20 and the mounting plate 12. Thus when the ostomy pouch 60 is coupled to the mounting plate assembly 10, the pouch 60 and the force transmitter member 20 are disposed between a thumb 100 and a forefinger 102, as shown in FIGS. 10–11. The forefinger 102 (FIG. 11) presses the coupling member 72 on the ostomy pouch 60 into engagement with the coupling member 18 while the thumb 100 pulls the force transmitter member 20 away from the mounting plate 12.

In this manner, the thumb 100 is used to apply a force through the force transmitter member 20 that is directed away from the mounting plate 12 and away from the abdominal surface 26. The force applied by the thumb 100 opposes the force of the forefinger 102 against the coupling member 72 to engage such coupling member with the coupling member 18. The force of the forefinger 102 is thus directed toward the abdomen 26. An opposing force through the force transmitter member 20 is thus used to neutralize the coupling force applied by the forefinger 102 against the coupling members 72 and 18. A resultant force directed toward the abdominal area 26 around the stoma 24 can thus be minimized.

Since the force transmitter member 20 is secured directly to the coupling member 18, a manual pulling force applied to the force transmitter member 20 by gripping the member 20 is transmitted through the coupling member 18, to offset or counter a force in the opposite direction imposed by the forefinger 102. The force transmitter member 20 is thus used to redirect, neutralize or counter the force applied to the coupling member 72 during engagement of the coupling members 18 and 72. Under this arrangement, neutralization of forces applied to the coupling members 18 and 72 during coupling can be easily accomplished.

As shown in FIG. 10, both hands of the user can be applied to the ostomy pouch 60 and the force transmitter member 20 during engagement of the pouch 60 to the mounting plate assembly 10.

Although FIG. 11 shows the thumb 100 between the force transmitter 20 and the mounting plate 12, it is a matter of choice by the user to use whichever fingers provide the most effective operation of the force transmitter member 20 and manipulation of the coupling members 18 and 72. For example, the finger position is reversed in FIG. 10.

During disconnection of the coupling members 18 and 72, the coupling member 72 is pulled away from the coupling member 18. A pulling force is thus directed away from the abdominal area 26. To counter or neutralize the force of disconnection a user may place one or more fingers against the abdominal area 26 at the mounting plate 12, thus bracing the abdominal area 26 and the mounting plate 12 against the oppositely directed disconnection force.

In some instances, it maybe desirable during disconnection of the ostomy pouch 60 to not only place the fingers against the abdominal area 26 but to also manipulate the force transmitter member 20 if further comfort can be obtained in such manner.

Some advantages of the invention evident from the foregoing description include a mounting plate assembly that has a force transmitter member affixed to a coupling element. The force transmitter member facilitates neutralization of forces passed through the coupling element when an ostomy pouch is coupled to the mounting plate assembly. A further advantage is that the force transmitter member is flexible and deflectable and does not interfere with the coupling process or alter the positioning of the coupling members. A further advantage of the invention is that the force transmitter member can be easily combined with the coupling member on the mounting plate assembly. Still another advantage of the invention is that the force transmitter member can be operated with one hand or both hands simultaneously to reduce or substantially neutralize forces that would normally be imposed on the abdominal area during coupling of the ostomy pouch to the mounting plate assembly.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A coupling device comprising,
    a) a flexible mounting plate having an opening for a stoma,
    b) a coupling member having an annular base flange, said base flange including an annular rim projecting therefrom, said base flange having a lower surface and upper surface, said entire lower surface being joined to said mounting plate,
    c) a flexible annular force transmitter member having an inside diameter portion and an outside diameter portion, said inside diameter portion being joined to said upper surface of said base flange around said annular rim, said outside diameter portion being freely deflectable toward and away from said mounting plate and being sized to permit annular gripping to transmit force through said force transmitter member to said annular rim.

2. The coupling device as claimed in claim 1 wherein said annular base flange is welded to said mounting plate.

3. The coupling device as claimed in claim 1 wherein said inside diameter portion of said force transmitter member is welded to said base flange.

4. The coupling device as claimed in claim 1 wherein said force transmitter member has a dished profile in cross-section such that said outside diameter portion projects away from said mounting plate.

5. The coupling device as claimed in claim 1 wherein said mounting plate has an outside periphery and the outside diameter portion of said force transmitter member is within the peripheral confines of said mounting plate.

* * * * *